United States Patent
Gencarelli et al.

(10) Patent No.: US 10,068,302 B2
(45) Date of Patent: Sep. 4, 2018

(54) INTEGRATING VIDEO INTO PATIENT WORKFLOWS

(71) Applicant: CERNER INNOVATION, INC., Kansas City, MO (US)

(72) Inventors: Marissa Georgina Gencarelli, Kansas City, MO (US); Musa Hindi, Lee's Summit, MO (US); Michael S. Antonelli, Kansas City, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 686 days.

(21) Appl. No.: 14/266,927

(22) Filed: May 1, 2014

(65) Prior Publication Data

US 2015/0228042 A1 Aug. 13, 2015

Related U.S. Application Data

(60) Provisional application No. 61/937,922, filed on Feb. 10, 2014.

(51) Int. Cl.
| | |
|---|---|
| G06Q 10/00 | (2012.01) |
| G06Q 50/22 | (2018.01) |
| G06Q 10/10 | (2012.01) |
| G06F 19/00 | (2018.01) |

(52) U.S. Cl.
CPC ............. *G06Q 50/22* (2013.01); *G06F 19/00* (2013.01); *G06Q 10/10* (2013.01)

(58) Field of Classification Search
CPC ...... G06Q 50/22; G06Q 50/24; G06F 19/322; G06F 19/3418
See application file for complete search history.

(56) References Cited

U.S. PATENT DOCUMENTS

| | | | | |
|---|---|---|---|---|
| 2001/0016822 A1* | 8/2001 | Bessette | ................. | G06Q 50/22 705/3 |
| 2003/0214582 A1* | 11/2003 | Takahashi | .......... | G01C 21/3647 348/116 |
| 2007/0078931 A1* | 4/2007 | Ludwig | .................. | G06Q 10/10 709/204 |
| 2008/0065422 A1* | 3/2008 | Weber | .................... | G06Q 10/06 705/3 |
| 2009/0147940 A1* | 6/2009 | Graves | ............. | H04M 3/42365 379/208.01 |

* cited by examiner

*Primary Examiner* — Reginald R Reyes
(74) *Attorney, Agent, or Firm* — Shook, Hardy & Bacon L.L.P.

(57) ABSTRACT

Embodiments of the present invention are directed to methods, systems, and computer storage media for providing embedded video communication within a clinician workflow. Chart requests provide clinician workflows associated with patients. Video requests initiate video communications between clinicians and interested parties. Embedded video communication windows are fully integrated with the clinician workflows and facilitate video communication via mobile devices between care teams, specialties, patients, and other interested parties. Clinicians may perform actions within the workflows while the video communications are in progress and available for viewing by the clinicians.

20 Claims, 15 Drawing Sheets

FIG. 4

McKinley, Bill
28yrs M  DOB: 08/08/1985

Chief Complaint

Sinus headache

Notes (7) — More Notes

| My Last Note | Since Last Time | |
|---|---|---|
| 06/12/2013 Admission Note-Physician Jefferson, Tom MD | 05/21/2013 General Madison, Jim MD | 05/21/2013 General Madison, Jim MD |

Today's Vitals & Measurements   US / Metric

| Temperature | Heart Rate | Respiratory Rate | Blood Pressure | Height |
|---|---|---|---|---|
| -- | -- | -- | -- | -- |

Problems [+]

Strep Throat
034.0

Diabetes

Hypertension
Patient Stated

Allergies [+]

Penicillin, Codeine, Peanuts

Laboratory Results

| General Hematology | Urine Macroscopic | Routine Chemistry |
|---|---|---|
| 3 months (4) | 1 month (1) | 1 month (21) |

Histories   Social | Family | Procedure

Tobacco
Type: Cigarettes. Amount: 2 pack per day. Ready to change: No.

Review | Order

FIG. 6

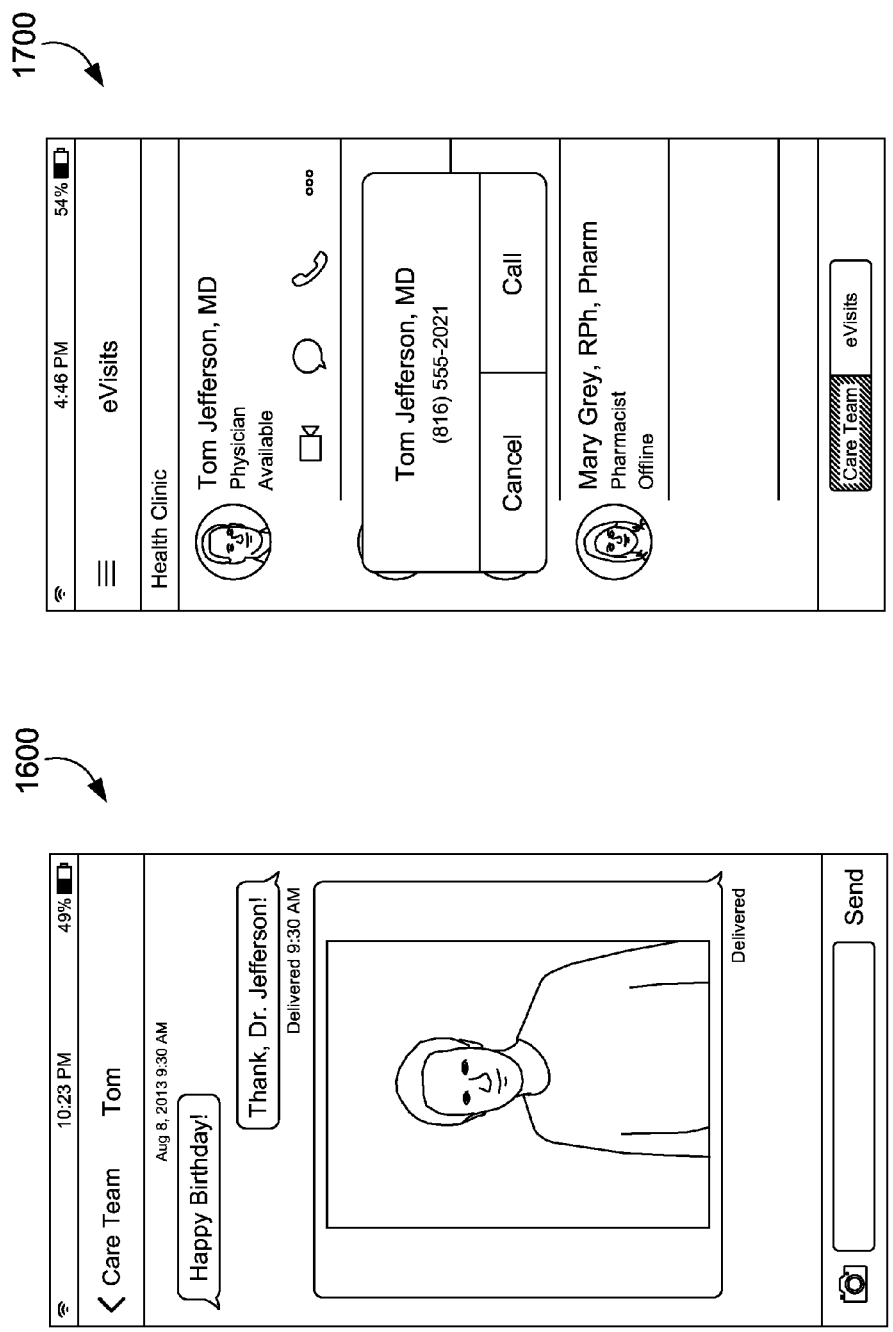

INTEGRATING VIDEO INTO PATIENT WORKFLOWS

CROSS REFERENCE TO RELATED APPLICATIONS

This application claims priority to U.S. provisional application 61/937,922, filed Feb. 10, 2014, which is hereby incorporated by reference.

BACKGROUND

Care providers provide patient care via care teams in both inpatient and outpatient experiences. Research has shown that nearly twenty percent of visits are lost due to no-shows. Typically, these are follow-up visits for a given illness or condition that, if something does go wrong, the patient is at risk for worse health than when the patient was initially seen for the associated illness or condition. Electronic visits or e-visits may provide convenience for a patient and potentially reduce no-shows. However, providing the proper context for the clinician is difficult since the clinician is required to switch between an e-visit application and the various workflow applications, or worse, utilize multiple devices to properly manage the e-visit.

SUMMARY

Embodiments of the present invention relate to a video infrastructure that can be consumed by multiple care teams in an integrated form. In accordance with some embodiments, video is fully integrated as an inpatient workflow and facilitates video communication between care teams, specialties, patients, and other interested parties. In embodiments, a seamless interface is provided within the clinician workflow that provides embedded video communication via a mobile device with a specialist, patient, or other interested party in the context of the workflow (e.g., an electronic medical record (EMR) associated with a patient) allowing a clinician to perform an action within the workflow while the video communication is in progress and available for viewing by the clinician.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter. The present invention is defined by the claims.

BRIEF DESCRIPTION OF THE DRAWINGS

The present invention is described in detail below with reference to the attached drawing figures, wherein:

FIGS. 3-19 depict illustrative screen displays, in accordance with exemplary embodiments of the present invention.

DETAILED DESCRIPTION

Figure 1:
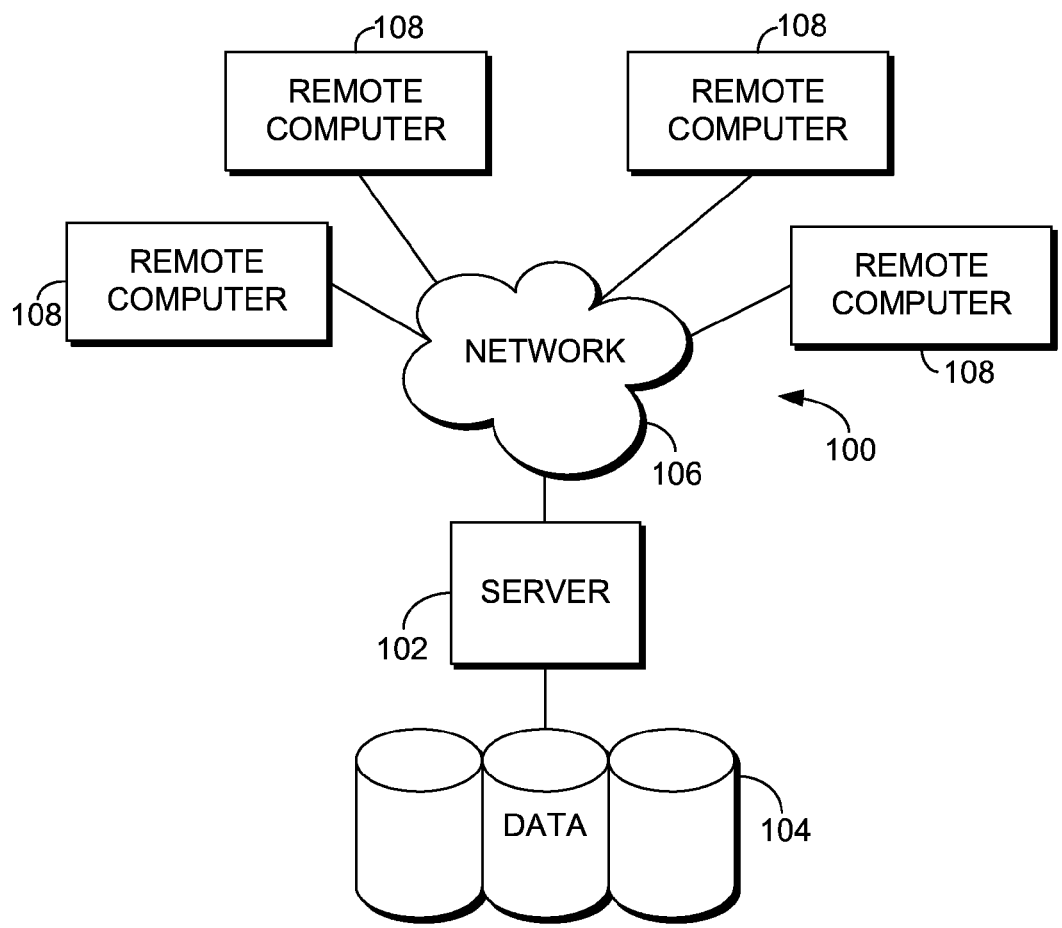
FIG. 1 is a block diagram of an exemplary computing environment suitable for use in implementing the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention are directed to methods, systems, and computer storage media for providing embedded video communication within a clinician workflow. Chart requests provide clinician workflows associated with patients. Video requests initiate video communications between clinicians and interested parties. Embedded video communication windows, provided within the clinician workflows, facilitate video communication between the clinicians and the interested parties.

Accordingly, one embodiment of the present invention is directed to one or more computer storage media having computer-executable instructions embodied thereon that, when executed by one or more computing devices, cause the one or more computing devices to perform a method of providing embedded video communication within a clinician workflow. A chart request is received from a clinician to provide a clinician workflow associated with a patient. A video request is received to initiate a video communication between the clinician and an interested party. An embedded video communication window is provided within the clinician workflow that facilitates the video communication between the clinician and the interested party.

Another embodiment of the present invention is directed to computer storage media having computer-executable instructions embodied thereon that, when executed by one or more computing devices, cause the one or more computing devices to produce a graphical user interface (GUI) for displaying embedded video communication within a clinician workflow. A visitor list display area displays a daily schedule for a clinician. The daily schedule includes a video communication indicator that identifies an interested party that has a video communication scheduled. A clinician workflow display area displays a workflow associated with the patient. The workflow includes a session indicator that the interested party has joined a session associated with the video communication. An embedded video display area displays a video communication associated with the interested party. The embedded video display area enables the clinician to minimize the size of the embedded video display area to allow the clinician to view the clinician workflow display area.

Yet another embodiment of the present invention includes a system for providing embedded video communication within a clinician workflow. The system includes one or more processors coupled to a computer storage medium, the computer storage medium having stored thereon a plurality of computer software components executable by the processor. A chart request component receives a chart request from a clinician to provide a clinician workflow associated with a patient. A video request component receives a video request to initiate a video communication between the clinician and an interested party. An embedded video component provides an embedded video communication window within the clinician workflow that facilitates the video communication between the clinician and the interested party.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Computer storage media does not comprise signals per se. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may comprise a treating physician or physicians; specialists such as intensivists, surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; students; and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

Figure 2:
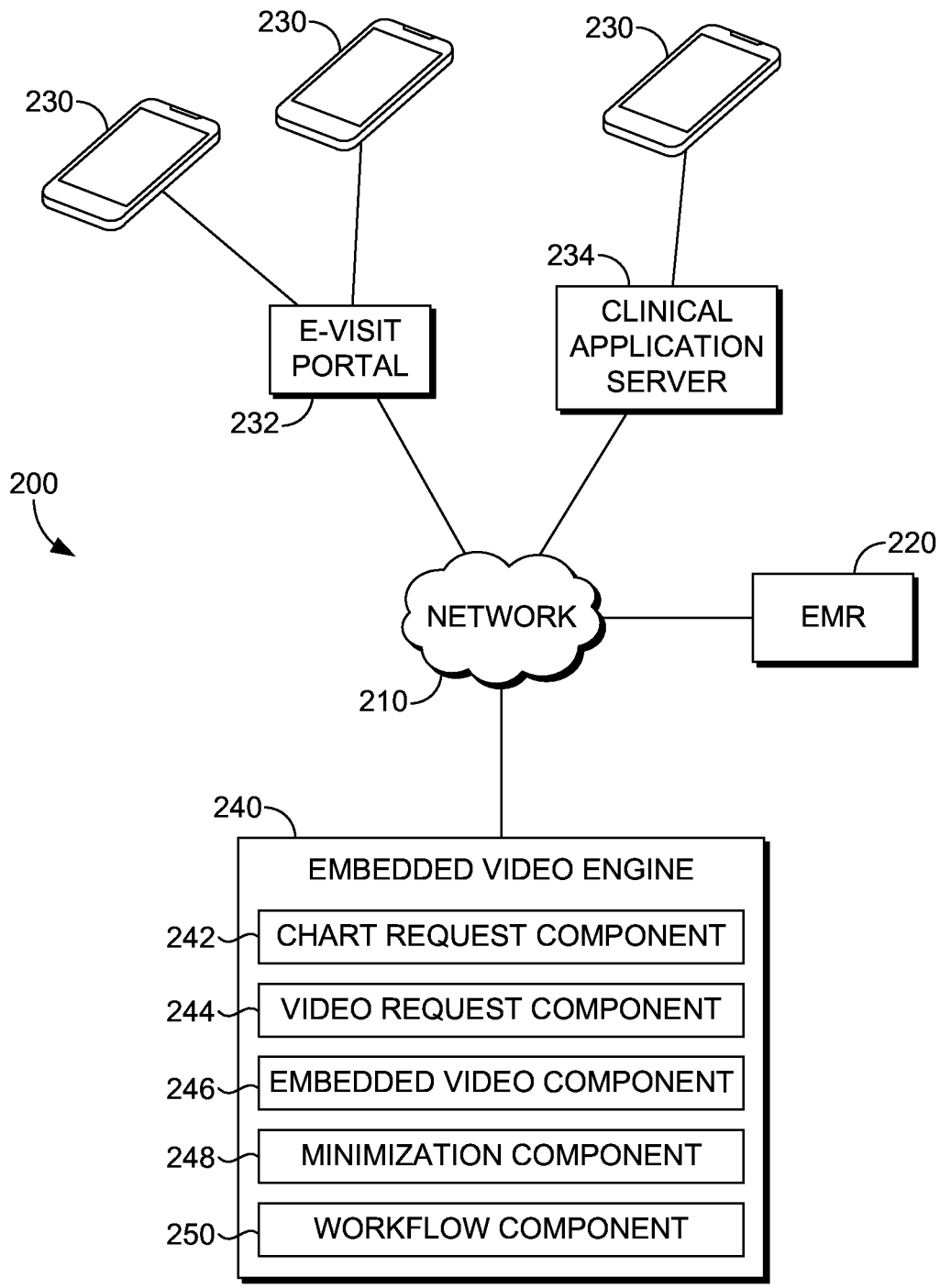
FIG. 2 is a block diagram of an exemplary system for providing embedded video communication within a clinician workflow suitable to implement embodiments of the present invention.

Turning now to FIG. 2, an exemplary computing system environment 200 is depicted suitable for use in implementing embodiments of the present invention. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes one or more display devices 230 (e.g., dashboard, computer, mobile device, and the like), clinical application server 234, electronic visit (e-visit) portal 232, embedded video engine 240, and EMR 220, all in communication with one another via a network 210. The network may include, without limitation, one or more secure local area networks (LANs) or wide area networks (WANs). The network may be a secure network associated with a facility such as a healthcare facility. The secure network may require that a user log in and be authenticated in order to send and/or receive information over the network.

In some embodiments, one or more of the illustrated components/modules may be implemented as stand-alone applications. In other embodiments, one or more of the illustrated components/modules may be distributed across multiple embedded video engines. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the embedded video engine might reside on a server, cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The clinical application server 234, the e-visit portal 232, and the EMR 220 are configured to provide and store information for use by, for example, the embedded video engine 240. The information stored in association with the clinical applications server, the patient portal, and the EMR is configured to be searchable for one or more items of information stored in association therewith. The information stored in association with the clinical application server, the patient portal, and the EMR may comprise information used by various components of the embedded video engine.

The EMR 220 may store EMRs of patients associated with one or more healthcare facilities. EMRs may comprise electronic clinical documents such as images, clinical notes, orders, summaries, reports, analyses, information received from application server and medical devices, or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, clinician assignments, and a host of other relevant clinical information.

The content and volume of such information in the clinical application server 234 and the EMR 220 are not intended to limit the scope of embodiments of the present invention in any way. Further, though illustrated as a single, independent component, the clinical application server and the EMR may, in fact, include a plurality of applications and/or storage devices, for instance, a database cluster.

The display devices 230 may be any type of devices capable of communicating via the network with the embedded video engine 240, the EMR 220, clinical application server 234, or medical devices. Such display devices may include any type of mobile and portable devices including cellular telephones, personal digital assistants, tablet PCs, smart phones, and the like.

The display of the display device 230 is configured to display information to the user of the display device (e.g., the clinician or interested party). The information may include communications initiated by and/or received by the embedded video engine 240, such as the video communication or information provided by the clinical application server 234 or the EMR 220. Embodiments are not intended to be limited to visual display but rather may also include audio presentation, visual presentation, combined audio/visual presentation, and the like.

Components of the context embedded video engine 240 may include a processing unit, internal system memory, and a suitable system bus for coupling various system components, including one or more data stores for storing information (e.g., files and metadata associated therewith).

The computing system environment 200 is merely exemplary. While the embedded video engine 240 is illustrated as a single unit, it will be appreciated that the embedded video engine is scalable. For example, the embedded video engine may in actuality include a plurality of computing devices in communication with one another. The single unit depictions are meant for clarity, not to limit the scope of embodiments in any form. Although the embedded video engine is illustrated as a stand-alone unit, it is contemplated the embedded video engine, or components of the embedded video engine, may also be integrated in, for example, the clinical application server or the patient portal.

As shown in FIG. 2, the embedded video engine 240 comprises, in various embodiments a chart request component 242, a video request component 244, an embedded video component 246, a minimization component 248, and a workflow component 250. In some embodiments, one or more of the components may be implemented as stand-alone applications. It will be understood that the components illustrated in FIG. 2 are exemplary in nature and in number and should not be construed as limiting. Any number of components may be employed to achieve the desired functionality within the scope of embodiments hereof.

Chart request component 242 receives a chart request from a clinician to provide a clinician workflow associated with a patient. The clinician workflow may be associated with an EMR 220 for the patient or a particular medical application. An identifier may be associated with the patient (or interested party) and the EMR 220 for that patient. The chart request may indicate the clinician is ready to accept a video request that has been communicated by an interested party, such as via the e-visit portal 232. The chart request may be made by selecting a patient from a visitor list, described below with reference to FIG. 3. In one embodiment, selecting the patient from the visitor list automatically initiates the chart request for the appropriate clinician workflow for that patient. In one embodiment, an active clinician workflow is already launched on the device of the clinician. In this instance, chart request component 242 acknowledges the active clinician workflow as the chart request. A person_id may be associated with the active clinician workflow that corresponds to an identifier of a patient. In another embodiment, the chart request may automatically be initiated when an interested party provides a video request to video request component 244. For example, a patient may provide the video request for a video communication with a clinician. Chart request component 242 acknowledges that someone other than the clinician provided the request and automatically retrieves the appropriate clinician workflow and launches or requests to launch the workflow on the device of the clinician. A clinician identifier may be retrieved from the existing application session with the clinical application server 234 that corresponds to a personnel identifier in the clinical system. The clinician identifier, along with the identifier for the patient verifies that not only is the correct patient in the video communication, but also the correct clinician.

Video request component 244 receives a video request to initiate a video communication between the clinician and an interested party. The video request may be communicated by the clinician or the interested party, such as via the e-visit portal 232 or the clinical application server 234. Video request component may receive an initial video request from the interested party, for example, when a patient checks in to the e-visit portal (i.e., by signing in or logging in to the portal). The patient may utilize an identity to check in which is associated to the identifier and the EMR of the patient. Video request component may notify the clinician when the patient is available for the video communication and wait for the clinician to join the communication or approve the communication. As described above, the clinician may join or approve the communication by selecting the patient from the visitor list or by providing the chart request to the chart request component 242, which may utilize the appropriate person_id corresponding to the chart that may already be visible, rather than selecting a patient.

Embedded video component 246 provides an embedded video communication window within the clinician workflow that facilitates the video communication between the clinician and the interested party. The embedded video communication within the clinician workflow allows the clinician to interact with the interested party while maintaining the appropriate context for the communication. Further, the clinician may complete a task or perform and action within the clinician workflow (e.g., place an order, sign, document, and the like). For example, a patient may have an e-visit scheduled with the clinician. The clinician may initiate a chart request for an EMR associated with that patient so the clinician is able to consult the EMR while the video communication window remains open. During the electronic visit, the clinician may need a different workflow associated with the patient (e.g., a different application). The clinician may initiate a chart request for that particular workflow or application while the embedded video communication window remains open. The embedded video component may allow portions of the video communication to be recorded, but may first prompt either party for authorization. In one embodiment, the embedded video component may allow either party to share or save portions of recorded video with parties to the video communication, other parties not included in the video communication, the EMR, or the clinical application server.

In one embodiment, minimization component 248 enables the clinician to minimize the embedded video communication window. This allows the clinician to more efficiently interact with the workflow by moving the embedded video communication to another location on the display device 230. If necessary, the minimization component 248 may also enable the clinician to maximize the video communication window to allow the clinician to more efficiently interact with the patient.

In one embodiment, workflow component 250 enables the clinician to complete a workflow within the clinician workflow while maintaining communication with the interested party via the embedded video communication window. For example, the clinician may determine that an order should be entered for the patient. The clinician is able to enter that order for the patient during the electronic visit while the embedded video communication window remains open and the clinician can interact simultaneously with both the patient and the workflow. In one embodiment, workflow component enables the clinician to share or save portions of the workflow with the interested party, with other parties not included in the video communication, the EMR, or the clinical application server.

With reference to FIGS. 3-19, illustrative screen displays for providing embedded video communication within a clinician workflow are provided. It is understood that each of the illustrative screen displays are connected logically, such that they comprise a user interface designed for providing embedded video communication within a clinician workflow. The screen displays may appear in any order and with any number of screen displays, without regard to whether the screen display is described or depicted herein.

Figure 3:
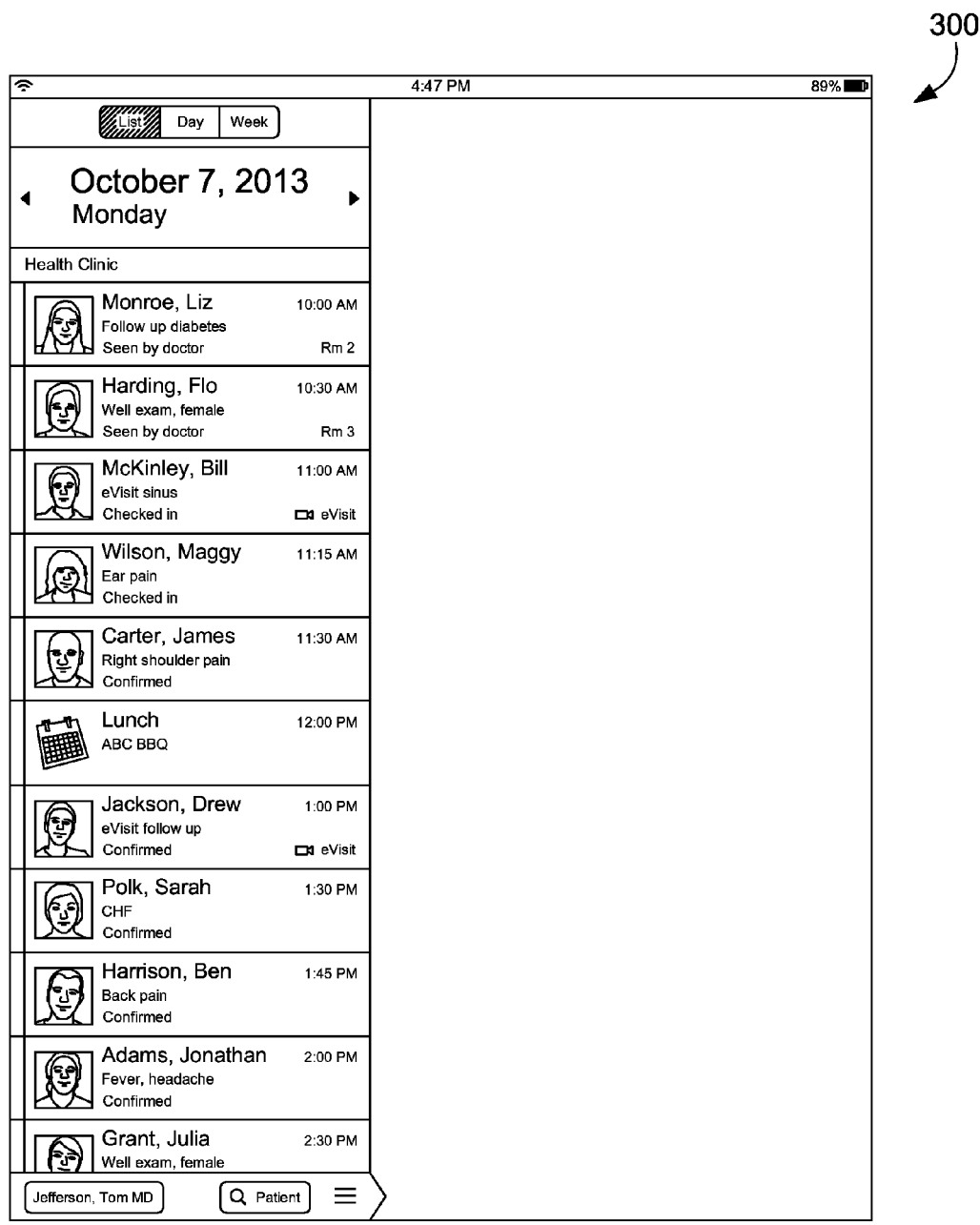

Referring now to FIG. 3, an illustrative screen display 300 of an embodiment of the present invention is shown. A visitor list display area displays a daily schedule for a clinician. The visitor list display area may be provided on a mobile device associated with a clinician once the clinician launches an application, such as an application provided by clinical application server 234 of FIG. 2. Similarly, the visitor list display area may be provided by the embedded video engine 240 of FIG. 2. The daily schedule may include a video communication indicator that identifies an interested party that has a video communication scheduled. In one embodiment, the visitor list display area may further display, within the daily schedule, a status indicator that identifies a status associated with the video communication. For example, the status may indicate that the interested party has checked in and is awaiting the clinician to approve or accept a request made by the interested party. The status may also indicate that the interested party has confirmed an electronic visit that is scheduled at a later time. Once the electronic visit has occurred, the status may indicate the interested party has already been seen or consulted.

Figure 4:
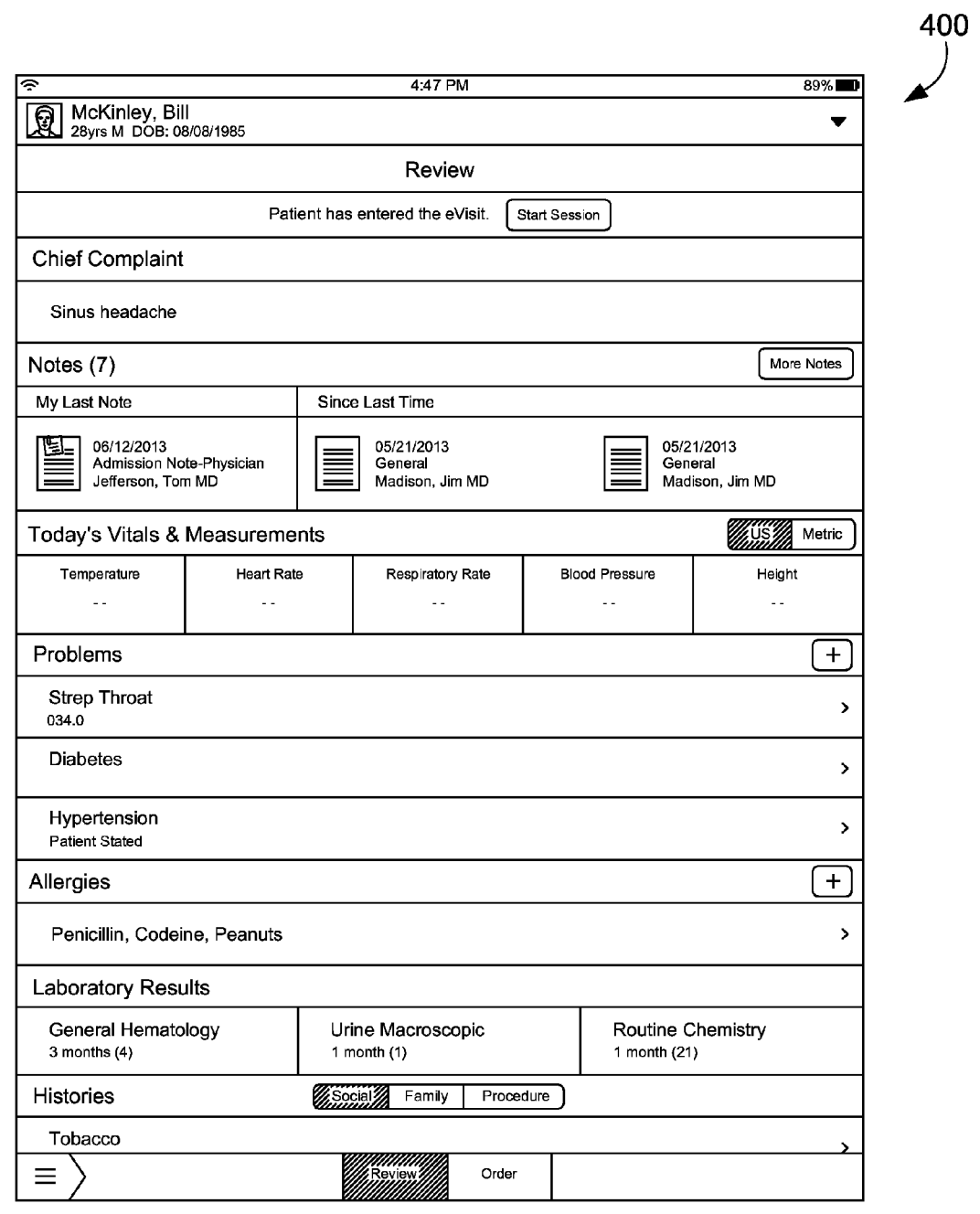

In FIG. 4, an illustrative screen display 400 of an embodiment of the present invention is shown. A clinician workflow display area displays a workflow associated with the patient. The workflow may include a session indicator that indicates the interested party has joined a session associated with the video communication. The session indicator may allow the clinician to begin the session.

Figure 5:
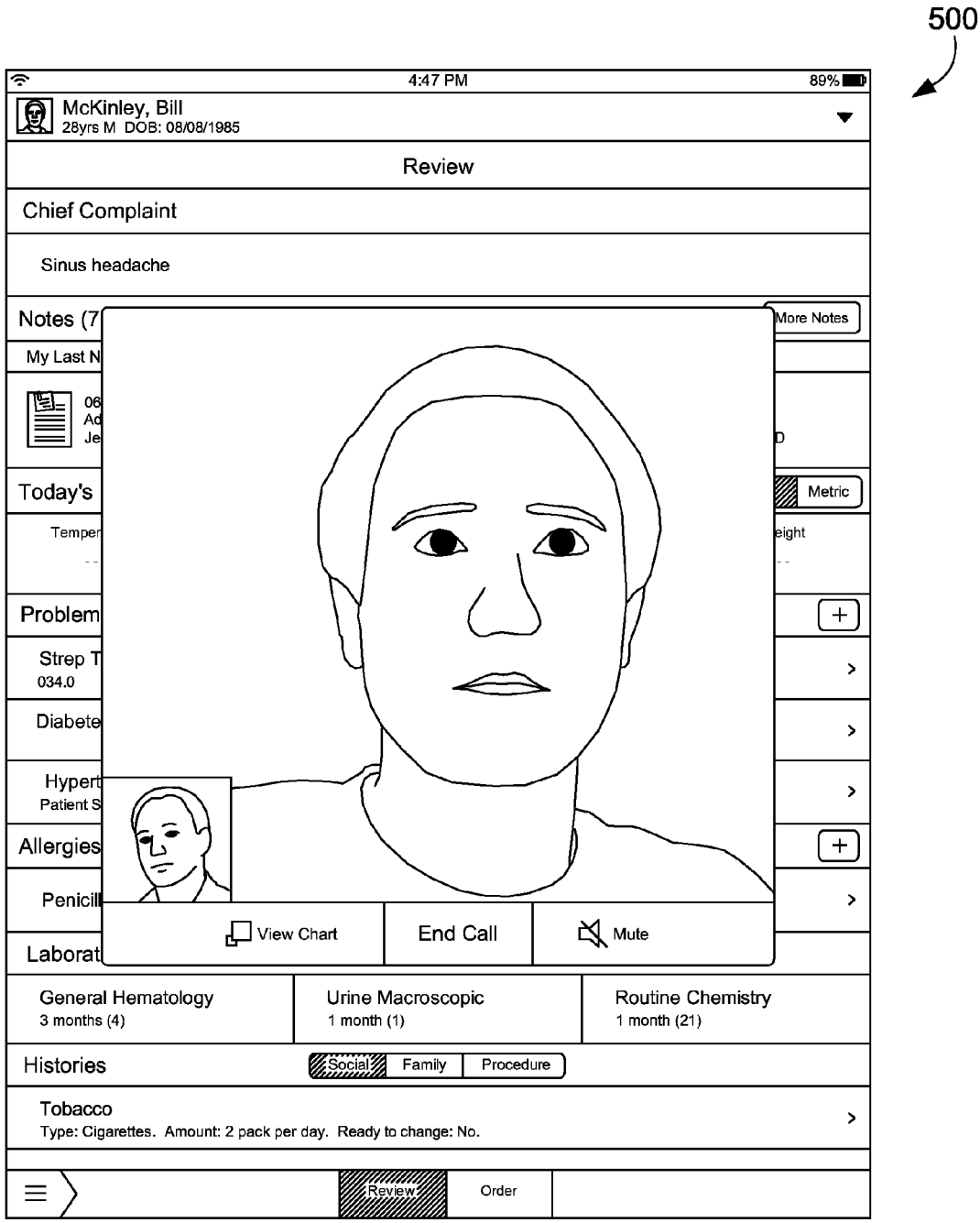

Turning now to FIG. 5, an illustrative screen display 500 of an embodiment of the present invention is shown. An embedded video display area displays a video communication associated with the interested party. The embedded video display area may display both the interested party via a camera on the mobile device associated with the interested party as well as the clinician (e.g., picture-in-picture display). This allows the clinician to view what is displayed on embedded video display area of the device associated with the interested party. The embedded video display area may also include controls to allow the clinician to view the workflow (which may minimize the embedded video display area), end the video communication, or mute the video communication.

Referring now to FIG. 6, an illustrative screen display 600 of an embodiment of the present invention is shown. As illustrated, the embedded video display area has been minimized and the clinician workflow display area is displayed more prominently. The embedded video display area may be automatically minimized when the clinician interacts with the clinician workflow display area (e.g., interacting with the view chart control) or by interacting with the display device (e.g., two-finger swipe). This may allow the clinician to better view and more efficiently interact with the clinician workflow display area. In addition to minimizing the size of the embedded video display area, the embedded video display area is moved into a tool bar or banner area of the clinician workflow display area, so the entire workflow is viewable and the clinician may freely interact with the workflow. In one embodiment, each of the display areas may be modified by size or location with the display area of the device according the preference of the clinician.

Figure 7:
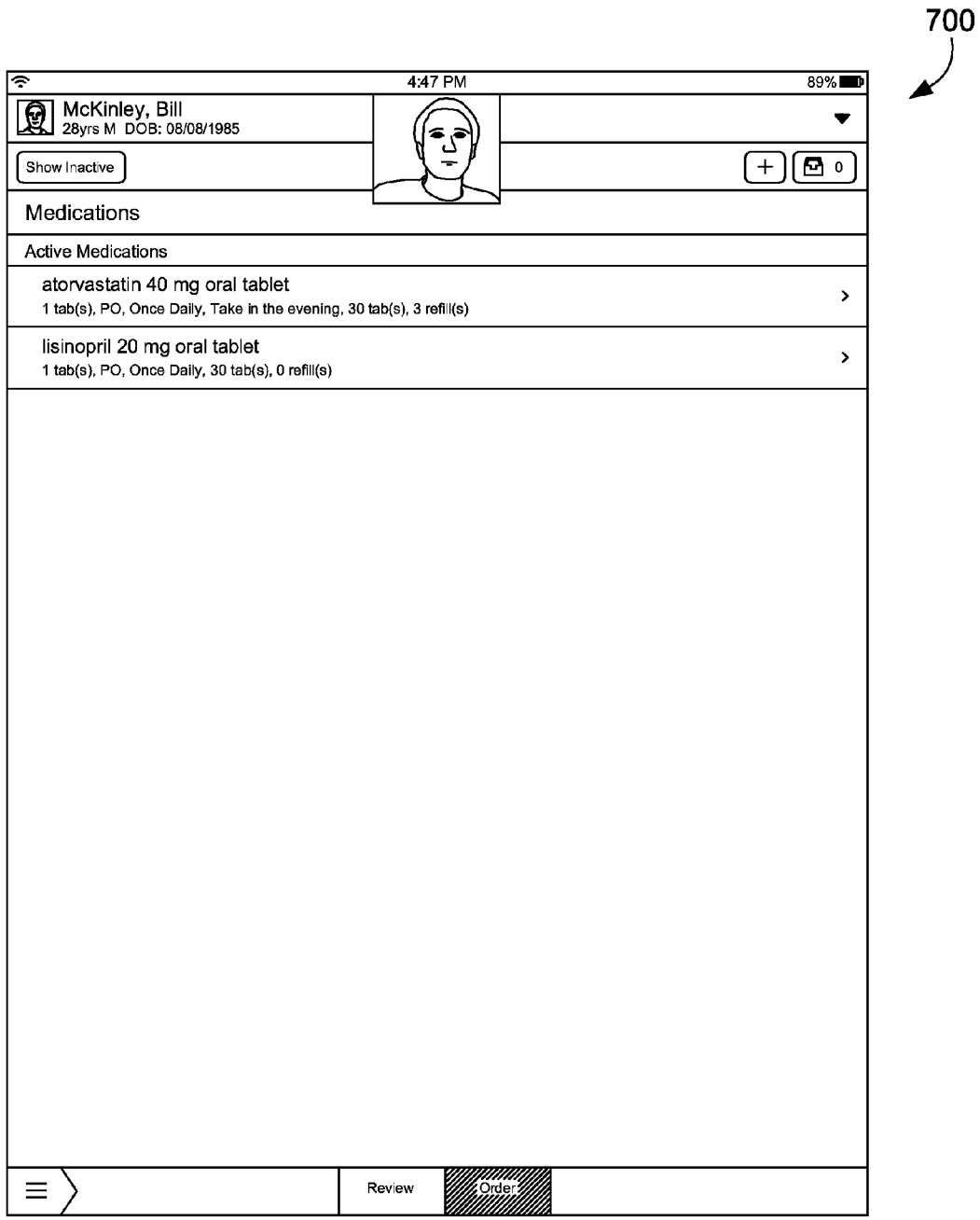

In FIG. 7, an illustrative screen display 700 of an embodiment of the present invention is shown. As illustrated, the clinician has interacted with a particular area of the workflow, changing the display of the clinician workflow area without interrupting the video communication. In this example, the clinician has selected to either review or place an order. From this workflow in the workflow display area, the clinician may input additional information (e.g., an order) while the video communication continues.

Figure 8:
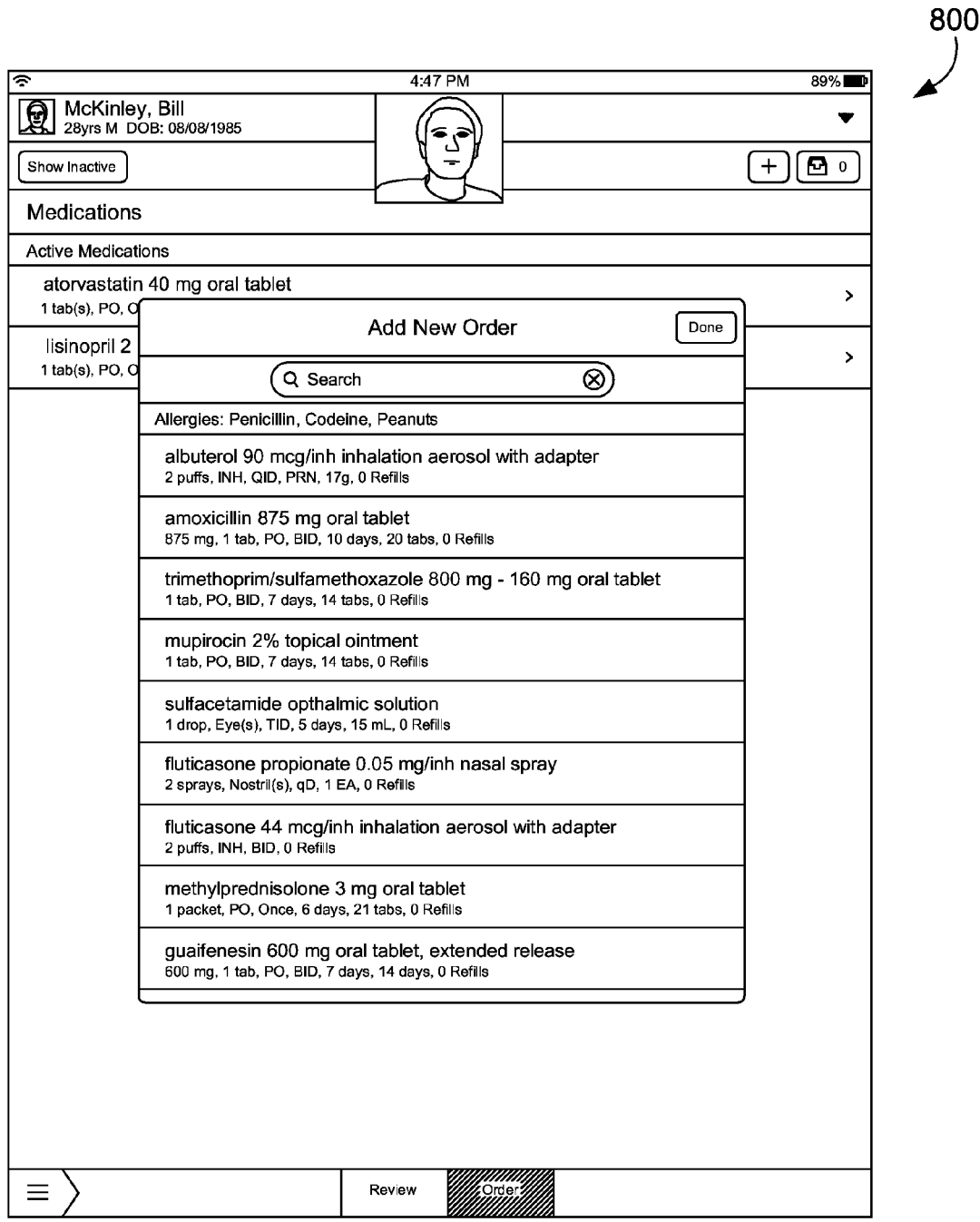

Turning now to FIG. 8, an illustrative screen display 800 of an embodiment of the present invention is shown. As illustrated, the clinician has determined to add a new order. This interaction again changes the display of the clinician workflow, enabling the clinician to complete a typical workflow, without interrupting the video communication.

Figure 9:
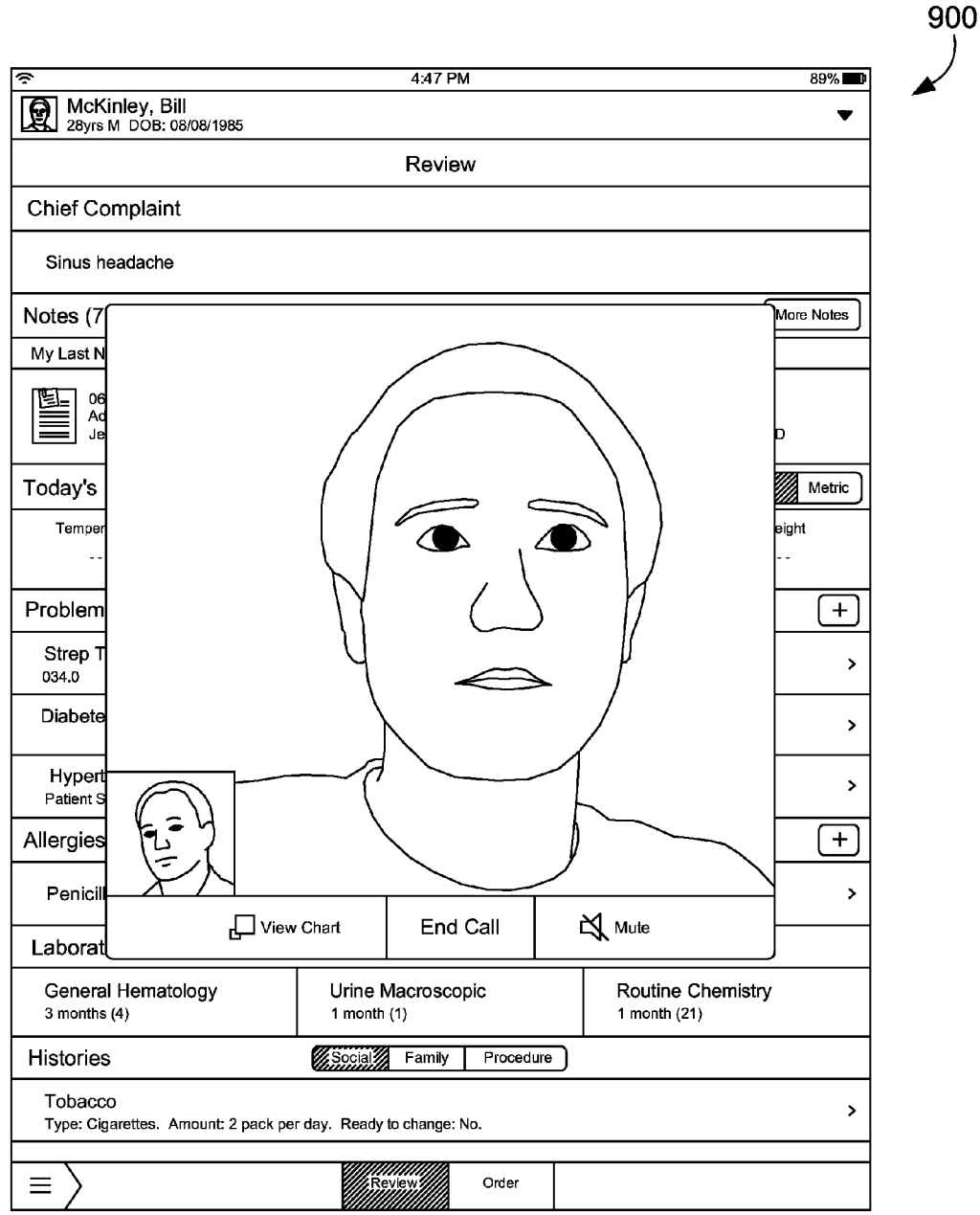

Referring now to FIG. 9, an illustrative screen display 900 of an embodiment of the present invention is shown. As illustrated, the embedded video display area has been maximized allowing the clinician to refocus on the patient. This may occur automatically based on an interaction received from the clinician (e.g., touching the embedded video display area, interacting with the mute control, or when the patient is interacting with the display on the device associated with the patient).

Figure 10:
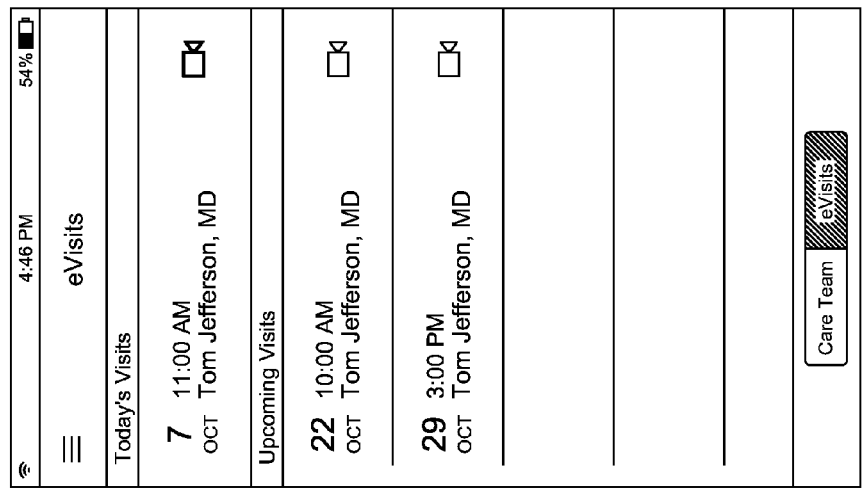

In FIG. 10, an illustrative screen display 1000 of an embodiment of the present invention is shown. An e-visit display area displays an e-visit list of upcoming e-visits that have been filtered out from the visitor list. The e-visit list may further allow the clinician to initiate a video request or approve one made by an interested party. Further, upon initiating or approving a video request from the e-visit list, a chart request may be automatically communicated to request the appropriate workflow for display on the device of the clinician.

Figure 11:
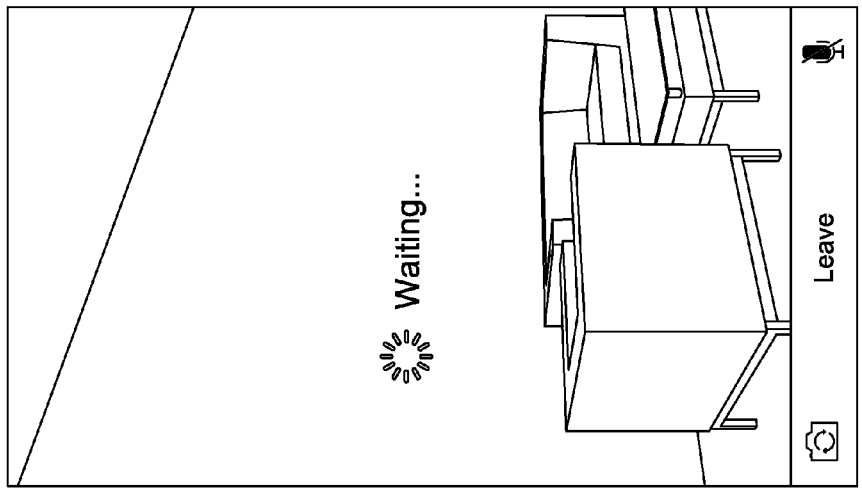

Turning now to FIG. 11, an illustrative screen display 1100 of an embodiment of the present invention is shown. As illustrated, the display of the device associated with the interested party indicates that a video request has been made. This causes the device of the provider to be notified so the provider can approve or join the video communication.

Figures 12, 13:
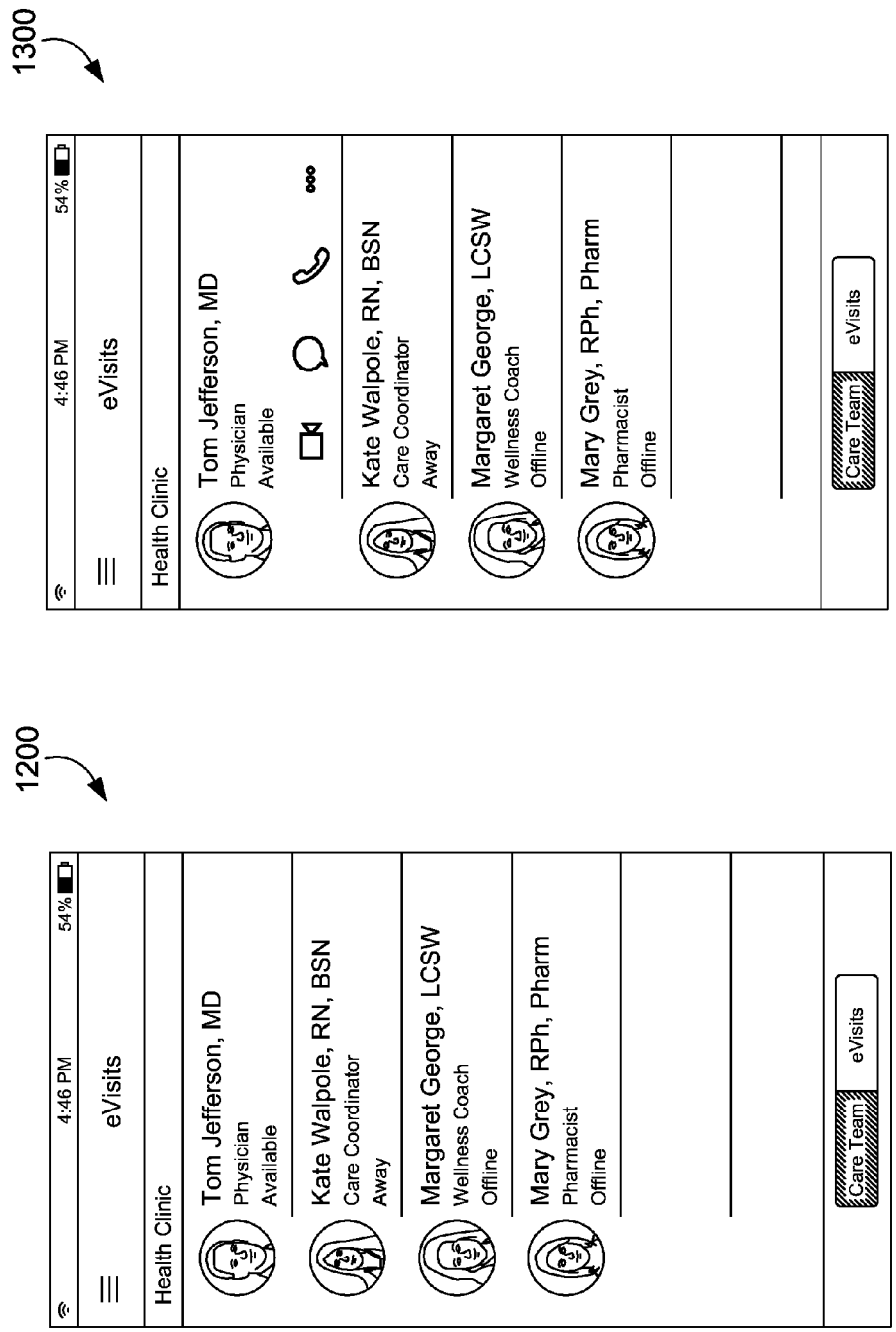

Referring now to FIG. 12, an illustrative screen display 1200 of an embodiment of the present invention is shown. As illustrated, a care team display area provides clinician associated with a care team for the patient. The care team display area may enable the interested party to initiate a video communication (i.e., provide a video request), send a text message, or call one or more of the care team clinicians.

In FIG. 13, an illustrative screen display 1300 of an embodiment of the present invention is shown. As illustrated, controls are displayed for care team clinicians that are available. Further, a status of each care team clinician may also be indicated.

Figure 14:
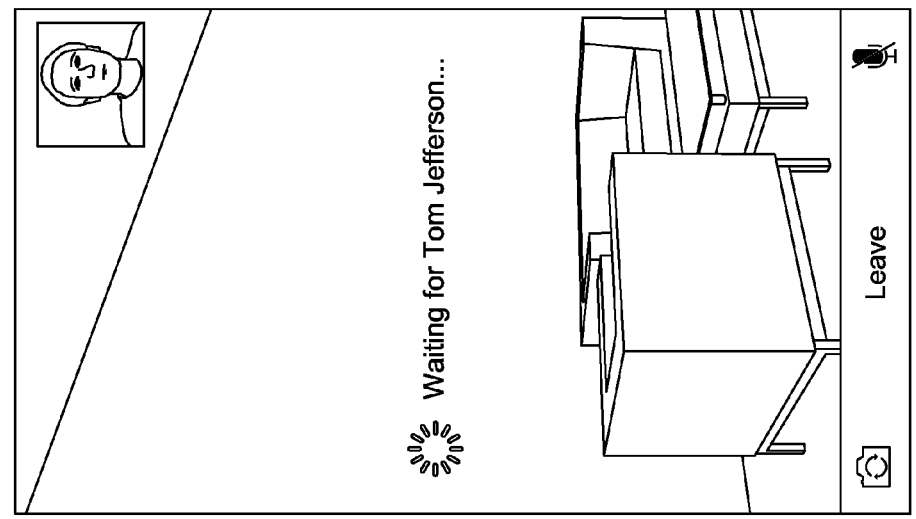

Turning now to FIG. 14, an illustrative screen display 1400 of an embodiment of the present invention is shown. Once a control has been selected, such as a video request for a particular care team member, the patient is placed into a virtual waiting room until the clinician approves or joins the video communication. The virtual waiting room may further allow the clinician to provide a status or instructions to the patient while the patient waits for the video communication to begin.

Figure 15:
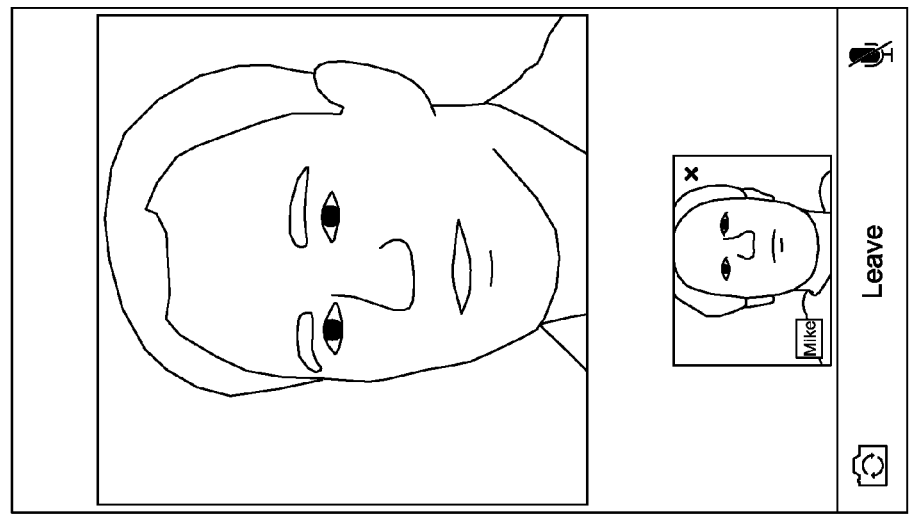

Referring now to FIG. 15, an illustrative screen display 1500 of an embodiment of the present invention is shown. As illustrated, a video display of each party to the video communication may be displayed on each display device. If one of the parties does not wish to view a self-video display, that party may close the self-display. Controls may allow each party to capture or communicate a photograph, leave the video communication, or mute the video communication.

Figures 18, 19:
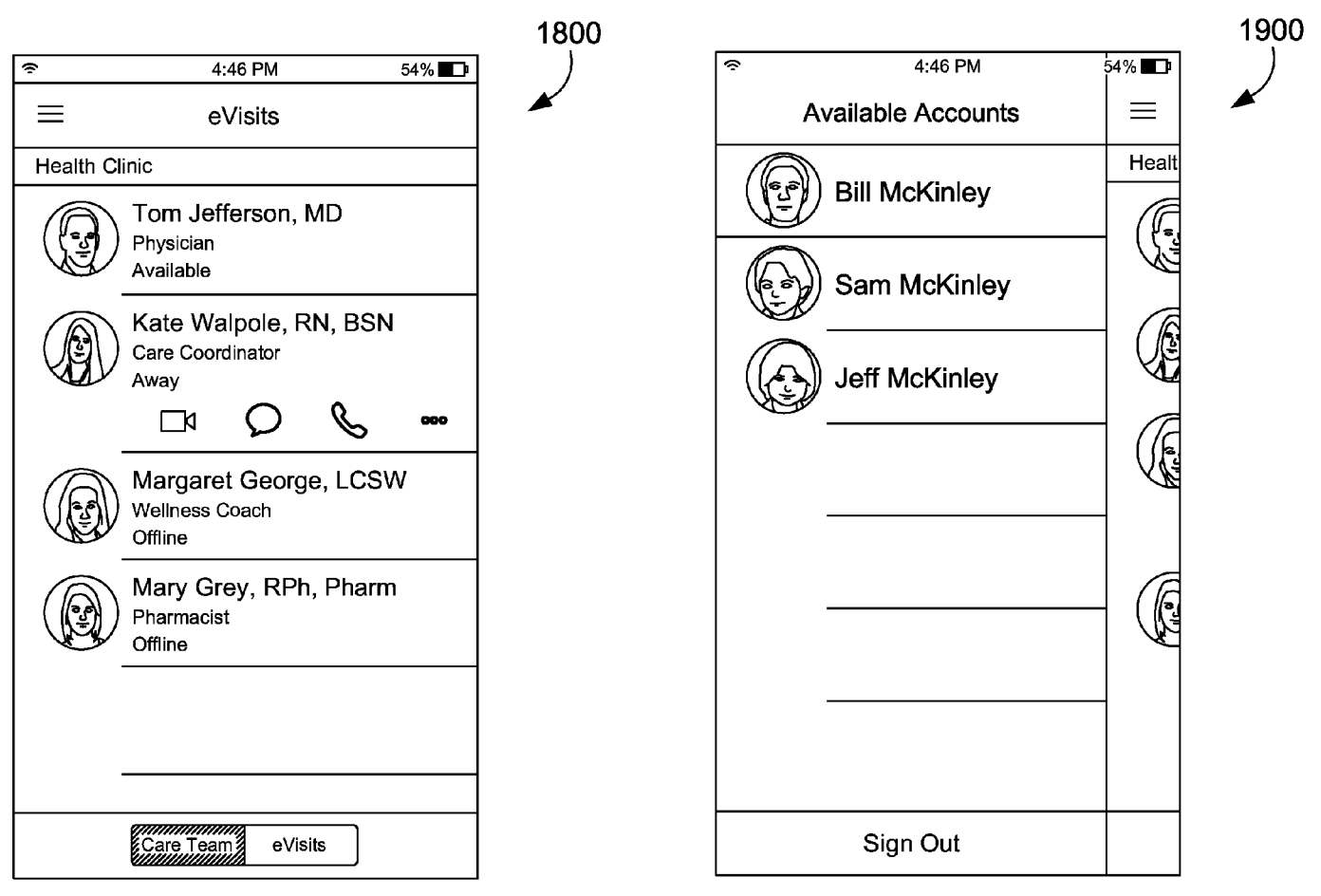

In FIGS. 16 and 17, an illustrative screen display 1600 of an embodiment of the present invention is shown. As illustrated in FIGS. 17 and 18, an interested party may communicate text messages or images to or initiate a voice communication with care team clinicians as described herein. The voice communication, text messages, or images may be communicated directly via the mobile device associated with the interested party while the interested party is logged into the patient portal. This allows the interested party to quickly identify and initiate the communication from the patient portal rather than having to look up contact information for the appropriate clinician.

Turning now to FIG. 18, an illustrative screen display 1800 of an embodiment of the present invention is shown. As illustrated, even when a particular care team clinician has a status that indicates that clinician is away or offline, the interested party may communicate text messages or images to or initiate a voice communication with the care team clinician by selecting or interacting with the appropriate control.

Referring to FIG. 19, an illustrative screen display 1900 of an embodiment of the present invention is shown. As illustrated, an interested party may switch between accounts associated with the current login credentials. For example, a parent may be logged in with an account that is associated with other family members. The parent may wish to log in on behalf of a child or participate in a video communication regarding another family member (or in addition to another family member). The parent may readily switch between accounts to participate in the appropriate video communication by selecting the desired account.

Figure 20:
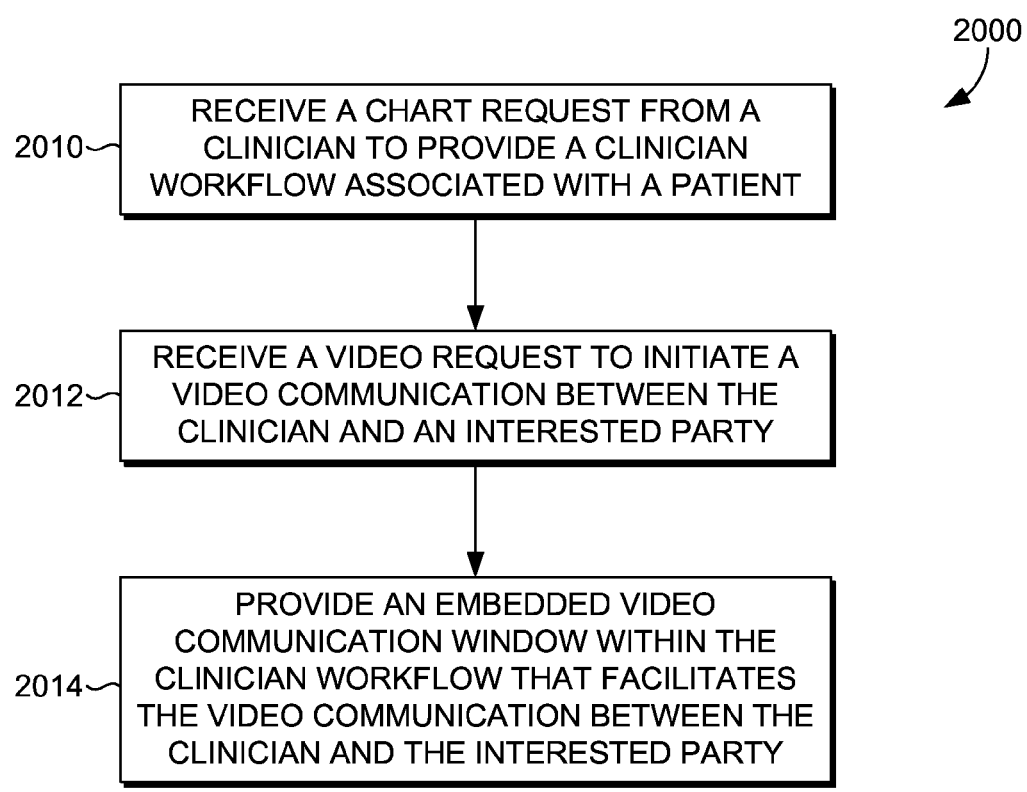
FIG. 20 is a flow diagram of an exemplary method of providing embedded video communication within a clinician workflow, in accordance with an embodiment of the present invention.

Referring now to FIG. 20, a flow diagram is illustrated showing an exemplary method 2000 of providing embedded video communication within a clinician workflow. As indicated at step 2010, a chart request is received from a clinician to provide a clinician workflow associated with a patient. In one embodiment, the clinician workflow is associated with an electronic medical record for the patient. In one embodiment, the clinician workflow is associated with a particular medical application.

A video request is received, at step 2012, to initiate a video communication between the clinician and an interested party. In one embodiment, the interested party is another clinician. In another embodiment, the interested party is the patient. In another embodiment, the interested party is a family member of the patient. In another embodiment, the interested party is associated with an insurer of the patient. In another embodiment, the interested party is multiple parties, such as any combination of the above.

In one embodiment, it is determined the interested party has joined the video communication. This may, in turn, prompt the clinician to join the video communication allowing the clinician any appropriate chart requests. Alternatively, the interested party may submit the request to initiate the video communication and it may be determined that the clinician has joined the video communication. In this instance, the clinician may be required to approve the request, or by joining the video communication may implicitly approve the request. Once it is determined the appropriate parties have properly joined the video communication, the video communication is enabled between the clinician and the interested party allowing the embedded video communication window to be provided, as described below.

At step 2014, an embedded video communication window is provided within the clinician workflow that facilitates the video communication between the clinician and the interested party. Providing the embedded video communication within the clinician workflow allows the clinician to interact with the interested party while maintaining the appropriate context for the communication. Further, this enables the clinician to complete a workflow within the clinician workflow. For example, a patient may have an electronic visit scheduled with the clinician. The clinician may initiate a chart request for an EMR associated with that patient so the clinician is able to consult the EMR while the video communication window remains open. Similarly, at some point during the electronic visit, the clinician may determine that an order should be entered for the patient. The clinician is able to enter that order for the patient during the electronic visit because the embedded video communication window is provided within the clinician workflow. Similarly, during the electronic visit, the clinician may need a different workflow associated with the patient (e.g., a different application). The clinician may initiate a chart request for that particular workflow or application while the embedded video communication window remains open.

In one embodiment, user input from the clinician is awaited. Such user input may be interacting with the clinician workflow, switching clinician workflows, requesting other clinician workflows, and the like. The user input may also be a request from the clinician to minimize or maximize the embedded video communication window. Minimizing the embedded communication window causes the embedded communication window to decrease in size and move to a portion of the display area so the clinician is able to interact with the clinician workflow. Similarly, maximizing the embedded communication window causes the embedded communication window to increase in size or move to a more prominent portion of the display area while still maintaining the context of the clinician workflow. This may allow the clinician to observe a condition or situation associated with the interested party. The embedded communication window may also allow the clinician to record video or photographs associated with the patient and save directly to the clinician workflow or share with another interested party (e.g., another clinician). Similarly, the embedded communication window may also allow the clinician to communicate items from the clinician workflow to the interested party (e.g., a prescription, directions, instructions, billing information, and the like).

The present invention has been described in relation to particular embodiments, which are intended in all respects to be illustrative rather than restrictive. Further, the present invention is not limited to these embodiments, but variations and modifications may be made without departing from the scope of the present invention.

It will be understood by those of ordinary skill in the art that the order of steps shown in method 2000 of FIG. 20 is not meant to limit the scope of the present invention in any way and, in fact, the steps may occur in a variety of different sequences within embodiments hereof. Any and all such variations, and any combination thereof, are contemplated to be within the scope of embodiments of the present invention.

What is claimed is:

1. One or more computer storage media having computer-executable instructions embodied thereon that, when executed by one or more computing devices, cause the one or more computing devices to perform a method of providing embedded video communication within a clinician workflow comprising, the method comprising:

receiving a chart request from a clinician to provide a clinician workflow associated with a patient, wherein the chart request is received from a mobile device associated with the clinician, the mobile device having a graphical user interface (GUI) enabled for video communication;

receiving a video request to initiate a video communication between the clinician and an interested party;

providing an embedded video communication window as part of the clinician workflow that facilitates the video communication between the clinician and the interested party, wherein the embedded video communication window and the clinician workflow share one display window to maintain context between the video communication and the clinician workflow, the one display window provided to the clinician via the GUI of the mobile device, wherein the embedded video communication window automatically adjusts in response to inputs to the clinician workflow by the clinician;

based on the communication between the clinician and the interested party, receiving an update to the clinician workflow to generate an updated clinician workflow; and saving at least a portion of the updated clinician workflow in an electronic medical record associated with the patient.

2. The one or more computer storage media of claim 1, further comprising determining the interested party has joined the video communication.

3. The one or more computer storage media of claim 2, further comprising prompting the clinician to join the video communication.

4. The one or more computer storage media of claim 3, further comprising enabling the video communication between the clinician and the interested party.

5. The one or more computer storage media of claim 1, further comprising minimizing the embedded video communication window.

6. The one or more computer storage media of claim 1, further comprising enabling the clinician to complete a workflow within the clinician workflow while the video communication between the clinician and the interested party remains open.

7. The one or more computer storage media of claim 1, wherein the clinician workflow is associated with an electronic medical record for the patient.

8. The one or more computer storage media of claim 1, wherein the interested party is one of another clinician, the patient, a family member of the patient, or associated with an insurer of the patent.

9. The one or more computer storage media of claim 1, further comprising receiving an order from the clinician while the video communication between the clinician and the interested party remains open.

10. The one or more computer storage media of claim 1, further comprising receiving a request to store at least a portion of the video communication in association with the clinician workflow.

11. The one or more computer storage media of claim 10, wherein the request to store the portion of the video communication comprises an authorization prompt from the clinician, the interested party, or both.

12. The one or more computer storage media of claim 1, wherein the embedded video communication window is movable about the clinician workflow.

13. Computer storage media having computer-executable instructions embodied thereon that, when executed by one or more computing devices, cause the one or more computing devices to produce a graphical user interface (GUI) for displaying embedded video communication within a clinician workflow, the GUI comprising:

a visitor list display area that displays a daily schedule for a clinician, the daily schedule including a video communication indicator that identifies an interested party that has a video communication scheduled;

a clinician workflow display area that displays a workflow associated with the patient, the workflow including a session indicator that the interested party has joined a session associated with the video communication; and an embedded video display area that is part of the clinician workflow display area and displays a video communication associated with the interested party, wherein the size of the embedded video display area is automatically minimized in response to inputs to the clinician workflow to allow the clinician to view the clinician workflow display area.

14. The GUI of claim 13, wherein the visitor list display area further displays within the daily schedule a status indicator that identifies a status associated with the video communication.

15. The GUI of claim 14, wherein the status includes checked in or confirmed.

16. The GUI of claim 13, further comprising a care team display area that provides clinicians associated with a care team for the patient, the care team display area enabling the interested party to initiate a video communication, send a text message, or call a care team clinician.

17. The GUI of claim 13, further comprising a consumer account display area that displays accounts associated with the interested party enabling the interested party to switch an account associated with the video communication.

18. A system for providing embedded video communication within a clinician workflow, the system comprising:

one or more processors coupled to a computer storage medium, the computer storage medium having stored thereon a plurality of computer software components executable by the processor, the computer software components comprising:

a chart request component that receives a chart request from a clinician to provide a clinician workflow associated with a patient, wherein the chart request is received from a mobile device associated with the clinician, the mobile device having a graphical user interface (GUI) enabled for video communication;

a video request component that receives a video request to initiate a video communication between the clinician and an interested party;

an embedded video component that provides an embedded video communication window as part of the clinician workflow that facilitates the video communication between the clinician and the interested party, wherein the embedded video communication window and the clinician workflow share one display window to maintain context between the video communication and the clinician workflow, the one display window provided to the clinician via the GUI of the mobile device, and wherein the embedded video communication window is automatically movable about the one display window in response to inputs to the clinician workflow by the clinician.

19. The system of claim 18, further comprising a minimization component that enables the clinician to minimize the embedded video communication window.

20. The system of claim 19, further comprising a workflow component that enables the clinician to complete a workflow within the clinician workflow while maintaining communication with the interested party via the embedded video communication window.

\* \* \* \* \*